United States Patent
Shefer et al.

(10) Patent No.: US 6,825,161 B2
(45) Date of Patent: Nov. 30, 2004

(54) MULTI COMPONENT CONTROLLED DELIVERY SYSTEM FOR SOAP BARS

(75) Inventors: Adi Shefer, Dayton, NJ (US); Samuel Shefer, Dayton, NJ (US)

(73) Assignee: Salvona LLC, Dayton, NJ (US)

(*) Notice: Subject to any disclaimer, the term of this patent is extended or adjusted under 35 U.S.C. 154(b) by 33 days.

(21) Appl. No.: 10/286,143

(22) Filed: Nov. 1, 2002

(65) Prior Publication Data

US 2003/0207776 A1 Nov. 6, 2003

Related U.S. Application Data

(63) Continuation-in-part of application No. 10/133,833, filed on Apr. 26, 2002, now Pat. No. 6,740,631.

(51) Int. Cl.$^7$ .............................................. C11D 17/08
(52) U.S. Cl. ...................... 510/438; 510/440; 510/441
(58) Field of Search ................................ 510/440, 441, 510/442, 438

(56) References Cited

U.S. PATENT DOCUMENTS

| | | | |
|---|---|---|---|
| 3,686,025 A | 8/1972 | Morton | 117/140 |
| 4,134,838 A | 1/1979 | Hooper et al. | 510/518 |
| 4,137,180 A | 1/1979 | Naik et al. | 510/522 |
| 4,152,272 A | 5/1979 | Young | 510/101 |
| 4,402,856 A | 9/1983 | Schnoring et al. | 428/402.22 |
| 4,446,032 A | 5/1984 | Munteanu et al. | 510/515 |
| 4,464,271 A | 8/1984 | Munteanu et al. | 510/515 |
| 4,749,501 A | 6/1988 | Nakagawa et al. | 510/130 |
| 4,767,457 A | 8/1988 | Ley et al. | 106/2 |
| 4,789,491 A | 12/1988 | Chang et al. | 510/525 |
| 4,803,195 A | 2/1989 | Holzner | 512/4 |
| 4,806,255 A | 2/1989 | Konig et al. | 510/522 |
| 4,919,841 A | 4/1990 | Kamel et al. | 252/186.26 |
| 4,937,370 A | 6/1990 | Sabatelli | 560/45 |

(List continued on next page.)

OTHER PUBLICATIONS

Federal Register, vol. 43, No. 166—Friday, Aug. 25, 1978, pp. 38206–38269.

Balassa, L et al., "Microencapsulation in The Food Industry", CRC Critical Reviews in Food Technology, pp. 245–265, Jul. 1971.

Barreto, Paul, "Perfumes for Specialties", Soap & Chemical Specialties, pp. 66–67 & 155, Dec. 1966.

Maleeny, Robert T., "Spray Dried Perfumes", Soap and San Chem, Jan. 1958, pp. 135–145.

Richmond, James M., "Cationic Surfactants", Marcel Dekker, Inc., New York and Basel, 1990, pp. iii–1.

*Primary Examiner*—John R. Hardee
(74) *Attorney, Agent, or Firm*—Mathews, Collins Shepherd & McKay, P.A.

(57) ABSTRACT

The present invention relates to an improved controlled delivery system that can be incorporated in soap bars to enhance deposition of active ingredients and sensory markers onto skin. The carrier system also provides controlled release or prolonged release of these actives from the skin over an extended period of time. The controlled delivery system of the present invention comprises substantially free-flowing, powder formed of solid hydrophobic, positively charged, nanospheres of encapsulated active ingredients, that are encapsulated in moisture sensitive microspheres. The high cationic charge density of the nanosphere improves deposition of active ingredients onto skin. The high cationic charge density on the nanosphere surface is created by incorporating a cationic conditioning agent into the solid hydrophobic matrix of the nanospheres, by incorporating a cationic charge "booster" in the moisture sensitive microsphere matrix, or by using a cationic conditioning agent in the nanosphere matrix in conjunction with a cationic charge "booster" in the microsphere matrix. The invention also pertains to soap products comprising the controlled release system of the present invention.

16 Claims, 1 Drawing Sheet

U.S. PATENT DOCUMENTS

| | | | |
|---|---|---|---|
| 4,946,624 A | 8/1990 | Michael | 510/101 |
| 4,954,285 A | 9/1990 | Wierenga et al. | 510/101 |
| 4,973,422 A | 11/1990 | Schmidt | 510/337 |
| 4,985,459 A | 1/1991 | Sunshine et al. | 514/561 |
| 4,999,786 A | 3/1991 | Mizutani et al. | 706/52 |
| 5,051,222 A | 9/1991 | Marten et al. | 264/143 |
| 5,066,419 A | 11/1991 | Walley et al. | 510/396 |
| 5,073,371 A | 12/1991 | Turner et al. | 424/401 |
| 5,073,372 A | 12/1991 | Turner et al. | 424/401 |
| 5,087,445 A | 2/1992 | Haffey et al. | 424/59 |
| 5,094,761 A | 3/1992 | Trinh et al. | 510/515 |
| 5,102,564 A | 4/1992 | Gardlik et al. | 427/394 |
| 5,112,688 A | 5/1992 | Michael | 428/402.2 |
| 5,126,061 A | 6/1992 | Michael | 510/106 |
| 5,137,646 A | 8/1992 | Schmidt et al. | 510/515 |
| 5,154,842 A | 10/1992 | Walley et al. | 510/523 |
| 5,174,911 A | 12/1992 | Lin et al. | 510/520 |
| 5,207,933 A | 5/1993 | Trinh et al. | 510/517 |
| 5,232,612 A | 8/1993 | Trinh et al. | 510/515 |
| 5,234,610 A | 8/1993 | Gardlik et al. | 510/327 |
| 5,234,611 A | 8/1993 | Trinh et al. | 510/523 |
| 5,236,615 A | 8/1993 | Trinh et al. | 510/349 |
| 5,246,603 A | 9/1993 | Tsaur et al. | 510/519 |
| 5,417,153 A | 5/1995 | King et al. | 99/517 |
| 5,425,887 A | 6/1995 | Lam et al. | 510/520 |
| 5,476,660 A | 12/1995 | Somasundaran et al. | 424/401 |
| 5,487,884 A | 1/1996 | Bissett et al. | 424/59 |
| 5,508,259 A | 4/1996 | Holzner et al. | 512/4 |
| 5,525,367 A | 6/1996 | King et al. | 426/533 |
| 5,723,420 A | 3/1998 | Wei et al. | 510/101 |
| 5,770,556 A | 6/1998 | Farrell et al. | 510/447 |
| 5,876,755 A | 3/1999 | Perring et al. | 424/489 |
| 5,955,409 A | 9/1999 | Farrell et al. | 510/141 |
| 6,024,943 A | 2/2000 | Ness et al. | 424/59 |
| 6,042,792 A | 3/2000 | Shefer et al. | 422/259 |
| 6,051,540 A | 4/2000 | Shefer et al. | 510/101 |
| 6,083,899 A | 7/2000 | Baker et al. | 510/515 |
| 6,248,703 B1 | 6/2001 | Finucane et al. | 510/152 |
| 6,395,302 B1 * | 5/2002 | Hennink et al. | 424/489 |
| 6,500,446 B1 * | 12/2002 | Derrieu et al. | 424/408 |

* cited by examiner

FIG. 1

MULTI COMPONENT CONTROLLED DELIVERY SYSTEM FOR SOAP BARS

This application is a continuation in part of U.S. Ser. No. 10/133,833, filed Apr. 26, 2002 now U.S. Pat. No. 6,740,631, the contents of which are hereby incorporated by reference into this application.

BACKGROUND OF THE INVENTION

1. Field of the Invention

The present invention relates to an improved controlled release carrier system that can be incorporated into soap bars that enhances deposition of active ingredients as well as fragrances onto skin and which prolongs the release of active ingredients and fragrances from the skin over an extended period of time.

2. Description of the Related Art

Consumer acceptance of soap bars is determined not only by the performance achieved with these products but the aesthetics associated therewith. Fragrance is an important aspect of the successful soap bars and they are being utilized, in addition to imparting an aesthetically pleasing odor, to convey to the consumer the product performance and effectiveness (i.e., the skin is clean, etc.). Recently, soap bars are utilized not only to clean and disinfect the skin, but also to impart long lasting malodor coverage and the performance features expected from these products are similar to those of deodorants.

Fragrances are typically added to soap bars to provide a fresh, clean impression for these products as well as the skin treated with these products. While the fragrance does not add to the performance of soap bars, it does make these products more aesthetically pleasing and the consumer has come to expect such products to have a pleasing odor. The fragrance plays a major, and often determining, role for the consumer in selecting and purchasing the soap bars. Consumers are becoming increasingly educated and expect a high level of sophistication in their soaps. Many consumers would prefer for the fragrance or the disinfecting actives, present in these products, to be deposited on the skin and remain there for an extended period of time to convey a lasting impression of freshness. Fragrance creation for soaps is restricted not only by considerations such as availability and cost, but also by compatibility of the fragrance ingredients with other components in the product composition and the ability of the fragrance ingredients to deposit onto the skin and survive the rinse process. Furthermore, large amount of fragrance is being lost during washing. Practice has shown that when currently available products are used, a large fraction of the fragrance is lost during the rinse process due to the solubility of certain fragrance ingredients in aqueous washing compositions, and the fraction of the fragrance which was deposited, quickly evaporates, due to the volatility of fragrance ingredients.

Water soluble polymers have also been used to encapsulate fragrance oils. Such capsules have proved useful in releasing perfume in deodorants. However, such capsules have not been commercially successful in extended release of perfume from skin. U.S. Pat. Nos. 5,770,556 and 5,955,409 disclose a process for making bar compositions having enhanced deposition of benefit agent. The patents relate to a process in which specific powder adjuvants comprising (a) benefit agents, (b) a carrier (e.g., soluble or partially soluble starches, water soluble amorphous solids or semi-crystalline water soluble solids), (c) water and (d) optional deposition/processing aids are first prepared and then mixed with bar chips prior to milling, extruding and stamping the bars. The carrier component disclosed by U.S. Pat. No. 5,770,556 is any water soluble starch including both partially soluble starches (such as corn or potato starch) and, more preferably, "true" water soluble starches, i.e., starches in which at least 10% by wt. or greater solution of starch in water will dissolve to form a clear or substantially clear solution. Examples of such include maltodextrin. The carrier may also be a semi-crystalline water soluble solid such as, for example, gelatin. The carrier compound generally will comprise about 15% to 98%, preferably 30% to 50% of the powder composition. These carrier materials will quickly dissolve in water (especially maltodextrins) to release the active and have little chance to enhance deposition of active ingredients onto the skin and sustain their release rate on the skin.

U.S. Pat. No. 5,876,755 discloses a water-sensitive matrix material which can be starch, modified starch, maltodextrin, cyclodextrin, gums, resins, synthetic or semisynthetic polymers such as polyvinyl pyrrolidine (PVP), polyvinylalcohol (PVA) and cellulose esters, and combinations of these materials. The preferred matrix material comprises modified starch. The encapsulating material (i.e. the encapsulated substance within the water-sensitive matrix) is conveniently prepared by spray drying, and is typically particulate so that the composition as a whole is particulate in nature.

U.S. Pat. Nos. 4,803,195 and 5,508,259 also disclose a water soluble encapsulation system that can be incorporated in soap bars. The matrix material utilized in the above patents comprises:

a. a solid film-forming substrate chosen from polyvinyl acetate, polyvinyl alcohol, dextrins, natural or modified starch, vegetable gums, pectins, xanthans, carboxymethylcellulose, methylcellulose, hydroxymethylcellulose and lipoheteropolysaccharides, and b. an emulsifying agent chosen from mono- or diglycerides of fatty acids, esters derived from the combination of fatty acids with sorbitol or a saccharide, or their alkoxylated derivatives, or an ester of tartaric, citric, ascorbic or lactic acid.

Again, these carrier materials will quickly dissolve in water (especially maltodextrins) to release the active and have little chance to enhance deposition of active ingredients onto the skin and sustain their release rate on the skin.

U.S. Pat. No. 4,749,501 discloses a solid soap composition comprising a soap base and microcapsules dispersed therein, said microcapsules are prepared by using a hydrophobic liquid as a core material, forming microcapsules by covering the hydrophobic liquid with coacervate of a hydrophilic material, and then adding an electrolyte to a solution having the microcapsules dispersed therein in an amount of 8 to 100 parts by weight to 100 parts by weight of the water used in the microcapsules to dehydrate the microcapsule films. The hydrophilic coacervate is an anionic hydrophilic high molecular weight substance is gum arabic, alkali metal salt of carboxymethyl cellulose, sodium alginate, carrageenan, styrene-maleic anhydride copolymer, methyl vinyl ether-maleic anhydride copolymer, acrylic acid copolymer, polyvinylbenzene sulfonic acid, carboxymethyl starch or mixtures thereof. The microcapsules hardly disintegrate during the soap production process but do disintegrate during the use of the soap composition when contacted with water. This type of controlled release system has the limitation of not working with all type of fragrance ingredients, especially not with fragrance ingredients that are relatively water-soluble and do not deposit into the skin.

A similar system is described in U.S. Pat. No. 6,248,703 which discloses bar compositions comprising a non-water soluble benefit agent core surrounded by a friable coating comprising the reaction product of (1) an amine selected from urea and melamine; and (2) an aldehyde selected from formaldehyde, acetaldehyde and glutaraldehyde; and mixtures of the amines and the aldehydes; wherein the capsules are strong enough to survive a soap extrusion process but sufficiently friable to break upon use of the bar by the consumer.

Perfumes have been adsorbed onto various materials such as silica and cyclodextrins to deliver perfume in soap bars. U.S. Pat. No. 5,723,420 discloses a personal cleansing bar compositions which contains a fragrance-releasing complex and a bar carrier. The fragrance-releasing complex contains a hydrophilic inorganic porous fragrance carrier and a fragrance impregnated within the fragrance carrier. Inorganic carriers include amorphous silica, precipitated silica, fumed silica and aluminosilicates such as zeolite and alumina. Another type of inorganic carrier suitable for use in the present invention include cyclodextrin. This system has the drawback that the fragrance oil is not sufficiently protected and is frequently lost or destabilized during processing.

Attempts to enhance deposition of fragrance onto skin have been described in U.S. Pat. No. 5,476,660 which discloses compositions to deposit an active substance on a target surface. The active substance is left on the surface after the product is rinsed off the surface. The preferred deposition is from compositions containing an anionic or nonionic active in the co-presence of an anionic surfactant. The compositions contain carrier particles having a zwitterionic or cationic surface and a plurality of outwardly protruding filaments containing charged organocarbyl groups. The term "zwitterionic" as described in this patent means a mixture of cationic and anionic (not necessarily neutral); thus the surface of the zwitterionic particles, have both cationic and anionic groups (i.e., positively charged and negatively charged organocarbyl groups). The filaments are formed from an emulsion comprising molten wax, an anionic surfactant and a cationic surfactant. The active substance is contained within the carrier particles.

The major challenge in designing controlled delivery systems for soap bars is maximizing the deposition of the system comprising the active ingredients onto the skin. There remains a need in the art for an efficient controlled delivery system, to effectively deposit active ingredients, as well as fragrances, onto skin and for a method to "boost" the overall charge density of particles thereby providing enhanced deposition onto the skin.

The prior art of which applicant is aware does not set forth a fragrance controlled release system that can be incorporated in a soap bar to enhance deposition of active ingredients, as well as fragrances, especially not for fragrance ingredients that are more soluble into the aqueous phase of the washing compositions and do not deposit onto the skin. There is also a need for a fragrance carrier system, for soap bars, that will allow using a wider range of fragrance ingredients that are currently not substantive on skin from a soap bar application and improved fragrance substantivity and longevity onto the skin. It is desirable to provide a control release system for overcoming these limitations. It is also desirable to provide a method using an efficient and economical process for effectively delivering a broad range of fragrances and other ingredients onto skin and yields a high impact fragrance "burst" upon washing and a prolonged fragrance release from the skin over an extended period of time.

SUMMARY OF THE INVENTION

The present invention relates to an improved controlled delivery system for active ingredients and sensory markers from soap bars, to enhance deposition of the active ingredients and sensory markers onto the skin and extend their release rate over a prolonged period of time. The controlled delivery system of the present invention is a multi-component system comprising of positively charged solid hydrophobic nanospheres encapsulated in a moisture sensitive microsphere. Active ingredients, as well as sensory markers such as fragrances, can be incorporated in the nanosphere matrix, in the microsphere matrix, or in both the nano and microsphere matrices. The nanosphere surface has high cationic charge density to improve the deposition of the nanospheres onto the skin. The high cationic charge density on the nanosphere surface is created by incorporating a cationic conditioning agent into the solid hydrophobic matrix of the nanospheres, by incorporating a cationic charge "booster" in the water sensitive microsphere matrix, or by using a cationic conditioning agent in the nanosphere matrix in conjunction with a cationic charge "booster" in the microsphere to matrix. The delivery system of the present invention also yields a high impact fragrance "burst" upon wash with the system and provides controlled release or prolonged fragrance release from the treated skin over an extended period of time.

In one embodiment, the present invention provides an improved fragrance carrier system for soap bars which has improved fragrance substantivity to bring the fragrance onto skin that has been washed with the soap bar comprising the fragrance carrier system. In the fragrance industry, the term "substantivity" refers to the deposition of the fragrance on the skin and the retention and perception of the fragrance on skin treated with the soap bar. The fragrance carrier system of the present invention provides cationic surface-active agents to allow a wide range of fragrances and fragrance ingredients to be compatible within the carrier composition and increase the substantivity of fragrances and fragrance ingredients that are currently not substantive on skin after wash with conventional soap bars. The fragrance-carrier system yields a high impact fragrance "burst" upon wash and provides prolonged fragrance release over an extended period of time. In addition, the production of the carrier system utilizes minimum processing steps and is efficient and economical.

The carrier system of the present invention is a free-flowing, powder formed of solid hydrophobic positively charged nanospheres comprising various active ingredients, as well as fragrances, that are encapsulated in a moisture sensitive microspheres, characterized by:

(i) protection of the active ingredients, as well as the volatile constituents of the fragrance, during storage, until needed;
(ii) yield high impact fragrance "burst" upon wash;
(iii) moisture triggered release of the nanospheres comprising the active ingredients, as well as the fragrance, in response to moisture (upon wash),
(iv) enhanced deposition of active ingredients and fragrances onto skin; and
(v) prolonged release of active ingredients and fragrances from the skin over an extended period of time.

The invention also provides a method for producing a multi component controlled release system of the present invention including active ingredients and a fragrance that comprises the steps of:

(i) incorporating a cationic conditioning agent, active ingredients, and fragrance into the solid hydrophobic nanospheres;
(ii) forming an aqueous mixture comprising of one or more active agents, a fragrance, the nanospheres, a cationic charge booster, and a moisture sensitive material, such as, starch derivatives, natural gums, polyvinyl alcohol, proteins, hydrocolloids, or mixture of thereof; and (iii) spray drying the mixture to form a dry powder composition.

The invention further provides a process for producing the multi component controlled release system of the present invention that comprises the steps of:

(i) heating hydrophobic materials to a temperature above the melting point of the materials to form a melt;
(ii) dissolving or dispersing a cationic conditioning agent into the melt;
(iii) dissolving or dispersing a first fragrance and a first active agent into the melt;
(iv) dissolving or dispersing a second active agent, a second fragrance, a cationic charge booster, and moisture sensitive material, such as, starch derivatives, natural gums, polyvinyl alcohol, proteins, hydrocolloids, or mixture of thereof, in the aqueous phase;
(v) heating the composition to above the melting temperature of the hydrophobic material;
(vi) mixing the hot melt with the aqueous phase to form a dispersion;
(vii) high shear homogenization of the dispersion at a temperature above the melting temperature until a homogeneous fine dispersion is obtained having a sphere size of from about 1 micron to about 2 microns;
(viii) cooling the dispersion to ambient temperature; and
(ix) spray drying the emulsified mixed suspension to form a dry powder composition.

The incorporation of spray dried nanospheres comprising fragrances and other active agents encapsulated within a moisture sensitive matrix in soap bars was found to enhance fragrance deposition onto skin, and to extend the release rate of these fragrances and active ingredients over an extended period of time. In an alternate embodiment, a controlled release composition is formed of hydrophobic nanospheres incorporating active agents. It has been found that a key to maximizing deposition of the system onto the skin is optimized particle size of the nanospheres of the present invention to ensure that the particles stay on the skin and have a sufficiently high cationic charge density on the particle surface to maximize ionic interaction between the particles and the skin.

It is believed that the cationic charge groups on the nanospheres surface become associated, in use of the composition, with the skin and assist in adhering the nanospheres onto skin during the wash through both sphere entrainment and electrostatic interactions to effectively deliver fragrance onto skin and sustain fragrance release rate. The hydrophobic matrix sustains the diffusion rate of the fragrance through the nanospheres and enables the fragrance to be released from the skin over an extended period of time.

The invention also provides soap bars comprising the multi component controlled release system of the present invention. Skin treated with a soap bar comprising the multi component controlled release system of the present invention was observed to exhibit a high level of fragrance (high odor intensity) and fragrance perception on skin (the level of fragrance and fragrance perception on skin) has been observed to perceived over an extended period of time, such as about 48 hours.

The present invention addresses the foregoing need to increase the deposition of wide range of fragrances and active ingredients onto skin and prolong their release so that the skin remains aesthetically pleasing for an extended period of time by employing an advanced carrier system to deposit the fragrance and other active ingredients onto the skin.

The carrier system of the present invention can be incorporated into any soap bar product and soap compositions and provide long-term storage stability.

DETAILED DESCRIPTION

Figure 1:
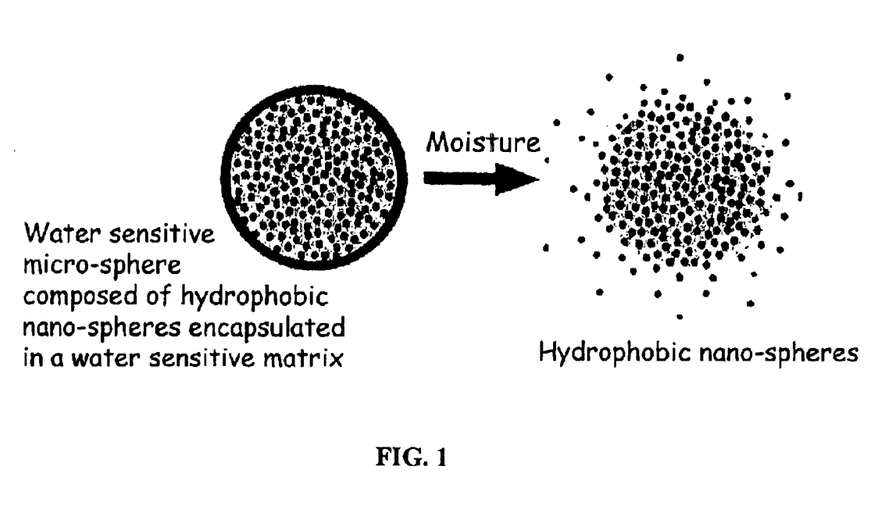
FIG. 1 is a schematic diagram of the controlled release system of the present invention upon contact with moisture.

The present invention features a method of controlling the release rate of an active agent, as well as fragrances in soap bars, yielding a high impact fragrance "burst" upon wash and providing fragrance release over an extended period of time. A multi component release system of the present invention is a free-flowing powder formed of solid hydrophobic, positively charged, nanospheres that are encapsulated in a moisture sensitive microsphere, as shown in FIG. 1. Active ingredients, as well as a fragrance, can be incorporated in the nanosphere matrix, in the microsphere matrix, or in both the nano and microsphere matrices. The microsphere can encapsulate the same or different active ingredients and fragrances. The high cationic charge density on the nanosphere surface improves deposition of the nanospheres onto skin. The high cationic charge density on the nanosphere surface is created by incorporating a cationic conditioning agent into the solid hydrophobic matrix of the nanospheres, by incorporating a cationic charge "booster" in the water sensitive microsphere matrix, or by using a cationic conditioning agent in the nanosphere matrix in conjunction with a cationic charge "booster" in the microsphere matrix. The term "spheres" is intended to describe solid, substantially spherical particulates. It will be appreciated that other shapes can be formed in accordance with the teachings of the present invention and are included in the term sphere.

The multi-component controlled release system of the present invention can comprise from about 1% to about 50% by weight hydrophobic matrix, from about 1% to about 50% by weight moisture sensitive matrix, from about 0% to about 10% by weight cationic charge booster, from about 0.01% to about 10% by weight cationic conditioning agents, from about 1% to about 50% by weight fragrance and from about 0% to 50% active ingredients. The microsphere can have an average sphere size in the range from about 20 microns to about 100 microns. The nanosphere can have an average sphere size in the range from about 0.01 micron to about 5 microns. The nanospheres can be formed of a hydrophilic matrix material having a melting point in the range from about 20 degrees C. to about 100 degrees C.

In the preferred embodiment, the active agent is present at a level from about 0.01% to about 60%, preferably from about 1% to about 50% by weight of the microsphere. In the preferred embodiment, the nanospheres are generally present in the water sensitive matrix at a level from about 1% to about 80%, preferably from about 1% to about 60% by weight of the matrix material with the balance being the active agents, the cationic conditioning agent, the cationic charge booster, and the water sensitive materials. In the preferred embodiment, the moisture sensitive matrix is generally present at a level from about 1% to about 80%, preferably from about 1% to about 60% by weight of the matrix material with the balance being the active agents, the cationic conditioning agent, the cationic charge booster, and the hydrophobic materials.

Nanospheres of the present invention can have an average diameter in the range from about 0.01 micron to about 10 microns. Preferably, the sphere size of the nanospheres is in the range from about 0.05 microns to about 2 microns. It has been found that spheres within the range of about 0.5 microns to about 1 micron are efficiently entrained on skin surface. This linear dimension for any individual sphere represents the length of the longest straight line joining two points on the surface of the sphere.

Additional components can be added to the carrier system or can be incorporated into either the nano or microsphere matrices. For example, additional components that can be included in the carrier system include cosmetic, dermatological, and pharmaceutical active agents. For example, the additional components that can be added to the controlled release system of the present invention including, but are not limited to: anti-oxidants; free radical scavengers; moisturizers; depigmentation agents; reflectants; humectants; anti-microbial (e.g., antibacterial) agents; allergy inhibitors; anti-acne agents; anti-aging agents; anti-wrinkling agents, antiseptics; analgesics; keratolytic agents; anti-inflammatory agents; fresheners; healing agents; anti infective; inflammation inhibitors; wound healing promoters; peptides, polypeptides and proteins; deodorants and antiperspirants; skin emollients and skin moisturizers; tanning agents; skin lightening agents; anti-fungals; depilating agents; counterirritants; poison ivy products; poison oak products; bum products; make-up preparations; vitamins; amino acids and their derivatives; herbal extracts; sensory markers (such as cooling agents, heating agents, and the like); skin conditioners; chelating agents; cell turnover enhancers; coloring agents; sunscreens; nourishing agents; moisture absorbers; sebum absorbers and the like; skin penetration enhancers; and other active ingredients. The additional components are usually present in an amount from about 1% to about 50% by weight of the nanospheres or microspheres.

I. Cationic Charge Booster

The controlled release system of the present invention can comprise a cationic charge booster to enhance the cationic charge density on the nanosphere surface. Suitable cationic charge boosters are described in U.S. Pat. No. 6,083,899 hereby incorporated by reference into this application. The preferred cationic charge boosters of the present invention are described herein below.

I.a. Quaternary Ammonium Compounds

A composition of the present invention comprises at least about 0.1%, preferably from about 0.1% to about 10%, more preferably from about 0.1% to about 5% by weight, of a cationic charge booster having the formula:

wherein $R_1$, $R_2$, $R_3$, and $R_4$ are each independently $C_1$–$C_{22}$ alkyl, $C_3$–$C_{22}$ alkenyl, $R_5$-Q-$(CH_2)_m$—, wherein $R_5$ is $C_1$–$C_{22}$ alkyl, and mixtures thereof, m is from 1 to about 6; X is an anion. Preferably $R_1$ is $C_6$–$C_{22}$ alkyl, $C_6$–$C_{22}$ alkenyl, and mixtures thereof, more preferably $R_1$ $C_{11}$–$C_{18}$ alkyl, $C_{11}$–$C_{18}$ alkenyl, and mixtures thereof; $R_2$, $R_3$, and $R_4$ are each prefer $C_1$–$C_4$ alkyl, more preferably each $R_2$, $R_3$, and $R_4$ are methyl.

Alternatively, $R_1$ can be a $R_5$-Q-$(CH_2)_m$— moiety wherein $R_5$ is an alkyl or alkenyl moiety having from 1 to 22 carbon atoms, preferably the alkyl or alkenyl moiety when taken together with the Q unit is an acyl unit. For example Q can be derived from a source of triglyceride selected from tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

An example of a softener cationic booster comprising a $R_5$-Q-$(CH_2)_m$— moiety has the formula:

wherein $R_5$-Q- represents oleoyl units and m is equal to 2.

Preferably X is a softener compatible anion, such as the anion of a strong acid. For example, X can be chloride, bromide, methylsulfate, ethylsulfate, sulfate, nitrate and mixtures thereof. More preferably X is chloride and methyl sulfate.

I.b. Polyvinyl Amines

A composition according to the present invention contains at least about 0.1%, preferably from about 0.1% to about 10%, more preferably from about 0.1% to about 5% by weight, of one or more polyvinyl amines charge boosters having the formula:

wherein y is from about 3 to about 10,000, preferably from about 10 to about 5,000, more preferably from about 20 to about 500. Polyvinyl amines suitable for use in the present invention are available from BASF under the name Lupasol® LU 321. The greater number of amine moieties per unit weight on the polyvinyl amines provides preferred substantial charge density.

I.c. Polyalkyleneimines

A composition of the present invention comprises at least about 0.1%, preferably from about 0.1% to about 10%, more preferably from about 0.1% to about 5% by weight, of a polyalkyleneimine charge booster having the formula:

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary-:secondary:tertary amine moieties of —$RNH_2$, —RNH, and —RN moieties, is 1:2:1. R can be $C_2$–$C_8$ alkylene, $C_3$–$C_8$ alkyl substituted alkylene, and mixtures thereof. R is ethylene, 1,2-propylene, 1,3-propylene, and mixtures thereof, and preferably ethylene. R radicals serve to connect the amine nitrogens of the backbone.

Optionally, one or more of the polyvinyl amine backbone —$NH_2$ unit hydrogens can be substituted by an alkyleneoxy unit having the formula:

wherein $R_1$ is $C_2$–$C_4$ alkylene; $R_2$ is hydrogen, $C_1$–$C_4$ alkyl, and mixtures thereof; and x is from 1 to 50. In one embodiment of the present invention the polyvinyl amine is reacted first with a substrate which places a 2-propyleneoxy unit directly on the nitrogen followed by reaction of one or more moles of ethylene oxide to form a unit having the general formula:

wherein x has the value of from 1 to about 50. Substitutions such as the above are represented by the abbreviated formula PO-EO$_x$—. However, more than one propyleneoxy unit can be incorporated into the alkyleneoxy substituent.

The preferred polyamine cationic charge boosters of the present invention comprise backbones wherein less than about 50% of the R groups comprise more than 3 carbon atoms. The use of two and three carbon spacers as R moieties between nitrogen atoms in the backbone is advantageous for controlling the charge booster properties of the molecules. More preferred embodiments of the present invention comprise less than about 25% moieties having more than 3 carbon atoms. Yet more preferred backbones comprise less than about 10% moieties having more than 3 carbon atoms. Most preferred backbones comprise about 100% ethylene moieties.

The cationic charge boosting polyamines of the present invention comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

However, not all of the suitable charge booster agents belonging to this category of polyamine comprise the above described polyamines. Other polyamines that comprise the backbone of the compounds of the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™ PR8515, having an average molecular weight of 1,800. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly nonamines, the cogenerically derived mixture does not appear to separate by distillation and can include other materials such as cyclic amines and particularly piperazines.

I.d. Poly-quaternary Ammonium Compounds

A preferred composition of the present invention comprises at least about 0.1%, preferably from about 0.1% to about 10%, more preferably from about 0.1% to about 5% by weight, of a cationic charge booster having the formula:

wherein R is substituted or unsubstituted $C_2$–$C_{12}$ alkylene, substituted or unsubstituted $C_2$–$C_{12}$ hydroxyalkylene; each $R_1$ is independently $C_1$–$C_4$ alkyl, each $R_2$ is independently $C_1$–$C_{22}$ alkyl, $C_3$–$C_{22}$ alkenyl, $R_5$-Q-$(CH_2)_m$—, wherein $R_5$ is $C_1$–$C_{22}$ alkyl, $C_3$–$C_{22}$ alkenyl, and mixtures thereof; m is from 1 to about 6; Q is a carbonyl unit as described above and mixtures thereof; X is an anion.

Preferably R is ethylene and $R_1$ is preferably methyl or ethyl, more preferably methyl. Preferably at least one $R_2$ is $C_1$–$C_4$ alkyl, more preferably methyl. Most preferably at least one $R_2$ is $C_{11}$–$C_{22}$ alkyl, $C_{11}$–$C_{22}$ alkenyl, and mixtures thereof.

Alternatively $R_2$ is a $R_5$-Q-$(CH_2)_m$— moiety wherein $R_5$ is an alkyl moiety having from 1 to 22 carbon atoms, preferably the alkyl moiety when taken together with the Q unit is an acyl unit derived from a source of triglyceride selected from the group consisting of tallow, partially hydrogenated tallow, lard, partially hydrogenated lard, vegetable oils, partially hydrogenated vegetable oils, such as, canola oil, safflower oil, peanut oil, sunflower oil, corn oil, soybean oil, tall oil, rice bran oil, and the like and mixtures thereof.

An example of a cationic booster comprising a $R_5$-Q-$(CH_2)_m$— moiety has the formula:

wherein $R_1$ is methyl, one of the $R_2$ units is methyl and the other of the $R_2$ unit is $R_5$-Q-$(CH_2)_2$ unit is $R_5$-Q-$(CH_2)_m$— wherein $R_5$-Q- is an oleoyl unit and m is equal to 2. X is a softener compatible anion, such as an anion of a strong acid. For example, X can be chloride, bromide, methylsulfate, ethylsulfate, sulfate, nitrate and mixtures thereof. More preferably chloride and methyl sulfate.

II. Cationic Conditioning Agents

The nanospheres of the present invention can comprise any of the cationic conditioning agents known in the art.

Hydrocarbon conditioners suitable for use herein are selected from the following classes of compounds:

(i) Cationic quaternary ammonium salts. The counterion is methyl sulfate or any alkyl sulfate or any halide. Examples of cationic quaternary ammonium salts include, but are not limited to:
(1) Acyclic quaternary ammonium salts having at least two $C_{8-30}$, preferably $C_{12-22}$ alkyl chains, such as: ditallowdimethyl ammonium methylsulfate, di(hydrogenated tallow)dimethyl ammonium methylsulfate, distearyldimethyl ammonium methylsulfate, dicocodimethyl ammonium methylsulfate and the like;
(2) Cyclic quaternary ammonium salts of the imidazolinium type such as di(hydrogenated tallow)dimethyl imidazolinium methylsulfate, 1-ethylene-bis(2-tallow-1-methyl) imidazolinium methylsulfate and the like;
(3) Diamido quaternary ammonium salts such as: methylbis(hydrogenated tallow amidoethyl)-2-hydroxyethyl ammonium methyl sulfate, methyl bis(tallowamidoethyl)-2-hydroxypropyl ammonium methylsulfate and the like;
(4) Biodegradable quaternary ammonium salts such as N,N-di (tallowoyl-oxy-ethyl)-N,N,-dimethyl ammonium methyl sulfate and N,N-di (tallowoyl-oxy-propyl)-N,N-dimethyl ammonium methyl sulfate. Biodegradable quaternary ammonium salts are described, for example, in U.S. Pat. Nos. 4,137,180, 4,767,547 and 4,789,491 incorporated herein by reference.

Preferred biodegradable quaternary ammonium salts include the biodegradable cationic diester compounds (See U.S. Pat. No. 4,137,180, incorporated herein by reference).
(ii) Tertiary fatty amines having at least one and preferably two $C_8$ to $C_{30}$, preferably $C_{12}$ to $C_{22}$ alkyl chains. Examples include hardened tallow-di-methylamine and cyclic amines such as 1-(hydrogenated tallow) amidoethyl-2-(hydrogenated tallow)imidazoline. Cyclic amines which may be employed for the compositions herein are described in U.S. Pat. No. 4,806,255 incorporated herein by reference.
(iii) Carboxylic acids having 8 to 30 carbons atoms and one carboxylic group per molecule. The alkyl portion has 8 to 30, preferably 12 to 22 carbon atoms. The alkyl portion may be linear or branched, saturated or unsaturated, with linear saturated alkyl preferred. Stearic acid is a preferred fatty acid for use in the composition herein. Examples of these carboxylic acids are commercial grades of stearic acid and palmitic acid, and mixtures thereof which may contain small amounts of other acids.
(iv) Esters of polyhydric alcohols such as sorbitan esters or glycerol stearate. Sorbitan esters are the condensation products of sorbitol or iso-sorbitol with fatty acids such as stearic acid. Preferred sorbitan esters are monoalkyl. A common example of sorbitan ester is SPAN 60 (ICI) which is a mixture of sorbitan and isosorbide stearates.
(v) Fatty alcohols, ethoxylated fatty alcohols, alkylphenols, ethoxylated alkylphenols, ethoxylated fatty amines, ethoxylated monoglycerides and ethoxylated diglycerides.
(vi) Mineral oils, and polyols such as polyethylene glycol.
(vi) Silicone oils and silicone surfactants as described in Lin et al., U.S. Pat. No. 5,174,911 and Lin et al. U.S. Ser. No. 07/776,719, incorporated herein by reference.

These softeners are more definitively described in U.S. Pat. No. 4,134,838 the disclosure of which is incorporated by reference herein.

Other quaternary ammonium salt conditioning compounds suitable for use are disclosed by Morton D. R. et al. in U.S. Pat. Nos. 3,686,025 and 6,083,899 are described in "Cationic Surfactants", Surfactant Science series, Vol. 34, edited by Richmond J. M., Marcel Dekker Inc., 1990, which are incorporated herein by reference.

The particularly preferred cationic conditioning agents for the carrier of the present invention are: behenyltrimethylammonium chloride; ditallowdimethylammonium methylsulfate; ditallowdimethylammonium chloride; methyl(1) stearylamidoethyl (2) stearylimidazolinium methosulfate; methyl(1)stearylamidoethyl(2)stearylimidazolinium chloride; N,N-di(tallowyl-oxy-ethyl)-N,N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium chloride; N,N-di(canolyl-oxyethyl)-N-methyl, N-(2-hydroxyethyl) ammonium chloride; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxoethyl)-N,N-dimethyl ammonium chloride; N,N,N-tri (tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; and 1,2-dicanolyloxy-3-N,N,N-trimethylammoniopropane chloride; and mixtures of thereof.

Methyl-1-tallowamidoethyl-2-tallowimidazolinium methylsulfate available from Witco Chemical Company under the name Varisoft™ 475. Examples of monoalkyltrimethylammonium salts are monotallowtrimethylammonium chloride, mono(hydrogenated tallow)trimethylammonium chloride, palmityltrimethyl ammonium chloride and soyatrimethylammonium chloride, available from Witco Chemical Company under the names Adogen™ 471, Adogen™ 441, Adogen™ 444, and Adogen™ 415, respectively. Examples of behenyltrimethylammonium chloride are commercially available under the name Kemamine™ Q2803-C from Humko Chemical Division of Witco Chemical Corporation. Methylbis(tallowamidoethyl)(2-hydroxyethyl) ammonium methylsulfate and methylbis(hydrogenated tallowamidoethyl)(2-hydroxyethyl)ammonium methylsulfate; are available from Witco Chemical Company under the names Varisoft™ 222 and Varisoft™ 110, respectively: dimethylstearylbenzyl ammonium chloride sold under the names Varisoft™ SDC by Witco Chemical Company and Ammonyx™ 490 by Onyx Chemical Company.

The most preferred cationic surface-active agents are cetyl trimethylammonium chloride and behenamidopropyl hydroxyethyl dimonium chloride under the name Incroquat Behenyl HE®, commercially available from Croda Inc.

In one embodiment of the present invention the nanosphere matrix is the cationic conditioning agent.

III. Matrix Materials for Forming the Nanospheres

Suitable solid core materials for forming nanospheres of the present invention are inert nontoxic hydrophobic materials with a melting point range between about 20 degrees C. and about 90 degrees C. Examples of hydrophobic materials include natural, regenerated, or synthetic waxes including animal waxes such as beeswax, lanolin and shellac wax, vegetable waxes such as carnauba, candelilla, sugar cane, rice bran, and bayberry wax, mineral waxes such as petroleum waxes including paraffin and microcrystalline wax, and mixtures thereof. Other hydrophobic materials which can be used in the present invention include wax and silicon copolymers, such as candelilla wax and silicone copolymer, ozokrite wax and silicon copolymers, beeswax and silicon copolymers, and the like. Other hydrophobic compounds which can be used in the present invention include: fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol, solid hydrogenated castor and vegetable oils, hard paraffins, hard fats, and mixtures thereof. Other hydrophobic compounds which can be used, include triglycerides, preferably of at least food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–C18), denoted medium chain triglycerides (MCT). The fatty acid moieties of such triglycerides can be unsaturated or polyunsaturated and mixtures of triglycerides having various fatty acid material. The nanosphere matrix can comprise a single hydrophobic material or a mixture of a plurality of materials. Other hydrophobic materials that are known to those skilled in the art and suitable materials as described in "Industrial Waxes," Vol. I and II, by Bennett F. A. I. C., published by Chemical Publishing Company Inc., 1975 and Martindale, "The Extra Pharmacopoeia", The Pharmaceutical Press, 28$^{th}$ Edition pp. 1063–1072, 1982 can be used in the present invention.

Other hydrophobic compounds which can be used in the present invention include synthetic polymers, such as alkylated polyvinylpyrrolidines, the Ganex® copolymer series, and ProLipids® 151 (commercially available from the ISP Company), Purester® series of materials (especially Purester® 24 and Purester® 34, vegetable derived esters produced from naturally derived fatty alcohol & methyl ester feedstocks which are non-GMO vegetable based renewable resources, commercially available from Strahl & Pitsch Inc. of West Babylon, N.Y.).

Examples of other suitable hydrophobic polymers and copolymer for use as the matrix material include polyethylene homopolymers A-C® 1702; A-C® 617, A-C® 617A, and A-C® 15, commercially available from Allied Signal Inc.; PERFORMALENE™ polyethylene homopolymer series commercially available from New Phase Technologies; PERFORMACOL™ linear primary alcohols series commercially available from New Phase Technologies; PERFORMACID™ linear saturated carboxylic acid series commercially available from New Phase Technologies; PERFORMA V™ polymer series commercially available from New Phase Technologies; ETHYLENE-ACRYLIC ACID COPOLYMERS A-C® 540, A-C® 540A, and A-C® 580 commercially available from Allied Signal Inc.; polyamides having a molecular weight in the range of from about 6,000 up to about 12,000, for example, MACROMELT™ 6030 manufactured by the Henkel Ag. of Dusseldorf, Germany; VERSALON™ 1135 polyamide polymer available commercially from General Mills, Inc It is preferred that the nanospheres of the present invention have a melting point in the range from about 20 degrees C. to about 90 degrees C., preferably from about 40 degrees C. to about 90 degrees C. The melting point of the spheres is usually a function of the carrier matrix employed. Accordingly, preferred matrix materials have a melting point in the range of about 50 degrees C. to about 80 degrees C., preferably from about 60 degrees C. to about 70 degrees C. It should be understood that it is the melting point of the sphere rather than of the carrier matrix that is important for use of the carrier system of the present invention.

Considerations in the selection of the matrix material include good barrier properties to the active agents and the fragrance ingredients, low toxicity and irritancy, stability, and high loading capacity for the active agents of interest.

IV. Matrix Materials for Forming a Microsphere Matrix

Water-sensitive materials for forming the microspheres of the present invention comprises of polyvinyl pyrrolidone, water soluble cellulose, polyvinyl alcohol, ethylene maleic anhydride copolymer, methyl vinyl ether maleic anhydride copolymer, polyethylene oxide, water soluble polyamide or polyester, copolymers or homopolymers of acrylic acid such as polyacrylic acid, polystyrene acrylic acid copolymers or starch derivatives, polysaccharide, hydrocolloid, natural gum, protein, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

The polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I–XIV of U.S. Pat. No. 5,051,222 issued on Sep. 24, 1991, the specification for which is incorporated by reference herein.

Polyvinyl alcohol useful for practice of the present invention is Mowiol® 3-83, having a molecular weight of about 14,000 Da and degree of hydrolysis of about 83%, Mowiol® 3-98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.; ELVANOL® 51-05, having a molecular weight of about 22,000–26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K. K., The Nippon Synthetic Chemical Industry Co., Ltd., of No. 9-6, Nozaki Cho, Kita-Ku, Osaka, 530 Japan.

Suitable polysaccharides are polysaccharides of the non-sweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

V. Active Ingredients

Vitamins

Various vitamins can be included in the controlled release system of the present invention. For example, vitamin A and derivatives thereof, vitamin $B_2$, biotin, pantothenic acid, vitamin K, vitamin D, vitamin E and mixtures thereof can be used.

Antimicrobial and Antifungal Actives

Antimicrobial and antifungal actives can be included in the controlled release system of the present invention. Antimicrobial and antifungal actives can be effective to prevent the proliferation and growth of bacteria and fungi and can be used in the controlled release system for stabilizing retinol of the present invention. Non-limiting examples of antimicrobial and antifungal actives include beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentarnidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; arnica extract (helenalin acetate and 11, 13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; capsicum frutescens extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydro-farnesol; dehydroacetic acid and its salts; dill seed oil; DOWICIL 200 (available from Dow Chemical, located in Midland, Mich.); echinacea; elenolic acid; epimedium; ethyl paraben; Fo—Ti; galbanum; garden bumet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; 1,6 hexanediol; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume; mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propyl paraben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; sphingosine; stevia; storax; sucrose esters; tarmic acid; tea; tea tree oil (cajeput oil); thyme; triclosan; triclocarban; tropolone; turpentine; umbelliferone (antifungal); yucca; and mixtures thereof.

Anti-inflammatory Agents

Anti-inflammatories can be included in the controlled release system of the present invention to enhance photoprotection benefits, particularly from UVA. Suitable steroidal anti-inflammatories include hydrocortisone; non-steroidal anti-inflammatories such as oxicans, salicylates, acetic acid derivatives, fenamates, propionic acid derivatives, pyrazoles, substituted phenyl compounds, 2-naphthyl containing compounds, and natural anti-inflammatories such as aloe vera. Examples of anti-inflammatories are described in U.S. Pat. No. 5,487,884, the entire contents of which are incorporated herein by reference.

Anti-acne Agents

Anti-acne agents can be included in the controlled release system of the present invention. Non-limiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids and bioflavonoids; bile salts such as scymnol sulfate and its derivatives, deoxycholate, and cholate; abietic acid; adapalene; allantoin; aloe extracts; arbietic acid and its salts; aryl-2,4 dioxo oxazolidine derivatives; ASEBIOL (available from Laboratories Serobiologiques, located in Somerville, N.J.); azaleic acid; barberry extracts; bearberry extracts; belamcanda chinensis; benzoquinolinones; benzoyl peroxide; berberine; BIODERMINE (available from Sederma, located in Brooklyn, N.Y.); bioflavinoids; bisabolol; S-carboxymethyl cysteine; carrot extracts; cassin oil; clove extracts; citral; citronellal; climazole; Completech MBAC-OS (available from Lipo); CREMOGEN M82 (available from Dragoco, located in Totowa, N.J.); cucumber extracts; dehydroacetic acid and its salts; dehydroeplandersterone salicylate; dichlorophenyl imidazoldioxolan which is commercially available as COMPLETECH MBAC-OS (from Lipo, located in Paterson, N.J.); DL valine and its esters; DMDM hydantoin; Epicutin TT (available from CLR); erythromycin; escinol; ethyl hexyl monoglyceryl ether; ethyl 2-hydroxy undecanoate; farnesol; farnesol acetate; geranoil; glabridin; gluconic acid; gluconolactone; glyceryl monocaprate; glycolic acid; grapefruit seed extract; gugu lipid; Hederagenin (available from Maruzen); hesperitin; hinokitol; hops extract; hydrogenated rosin; 10 hydroxy decanoic acid; ichtyhol; interleukin 1 alpha antagonists; iodo-2-propynyl butyl carbamate; Kapilarine (available from Greentech); ketoconazole; lactic acid; lemon grass oil; Lichochalcone LR15 (available from Maruzen); linoleic acid; LIPACIDE C8CO (available from Seppic, located in Paris, France); lovastatin; 4 methoxysalicylic acid; metronidazole; minocycline; mukurossi; neem seed oil; vitamin $B_3$ compounds (such as niacinamide and nicotinic acid); nisin; 5-octanoly salicylic acid; octopirox; panthenol; 1-pentadecanol; peonia extract; peppermint extract; phelladendron extract; 2-phenyl-benzothiophene derivatives; phloretin; PHLOROGINE (available from Secma); phosphatidyl choline; proteolytic enzymes; quercetin; red sandalwood extract; resorcinol; rosemary extract; rutin; sage extract; salicin; salicylic acid; skull cap extract; siber hegner extract; siberian saxifrage extract; silicol; sodium lauryl sulfate; sodium sulfoacetamide; Sophora Extract (available from Maruzen); sorbic acid; sulfur; sunder vati extract; tea tree oil; tetracyline; tetra hydroabietic acid; thyme extract; tioxolone; tocopherol; trehalose 6-undecylenoate; 3 tridecene-2-ol; triclosan; tropolone; UNITRIENOL T27 (available from Unichem, located in Gouda, Netherlands); vitamin $D_3$ and its analogs; white thyme oil; willow bark extract; wogonin; Ylang Ylang; zinc glycerolate; zinc linoleate; zinc oxide; zinc pyrithione; zinc sulfate and mixtures thereof.

Non-steroidal Cosmetic Soothing Actives

Cosmetic actives can be included in the controlled release system of the present invention. Cosmetic soothing actives can be effective in preventing or treating inflammation of the skin and can be included in the controlled release system of the present invention. The soothing active enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency. Non-limiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Non-limiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucolic acid, absinthium, acacia, aescin, alder buckthorn extract, allantoin, aloe, APT (available from Centerchem), arnica, astragalus, astragalus root extract, azulene, Baicalin SR 15 (available from Barnet Products Dist.), baikal skullcap, baizhu, balsam canada, bee pollen, BIOPHYTEX (available from Laboratories Serobiologiques), bisabolol, black cohosh, black cohosh extract blue cohosh, blue cohosh extract, boneset, borage, borage oil, bradykinin antagonists, bromelain, calendula, calendula extract, Canadian Willow-bark Extract (available from Fytokem), candelilla wax, Cangzhu, canola phytosterols, capsicum, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (available from Croda), darutoside, dehurian angelica, devil's claw, divalent metals (such as, magnesium, strontium, and manganese), doggrass, dogwood, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, feverfew, ficin, forsythia fruit, Fytosterol 85 (available from Fytokem), ganoderma, gaoben, Gatuline A (available from Gattefosse), gentian, germanium extract, gingko bilboa extract, ginkgo, ginseng extract, goldenseal, gorgonian extract, gotu kola, grape fruit extract, guaiac wood oil, guggal extract, helenalin esters, henna, honeysuckle flower, horehound extract, horsechestnut, horsetail, huzhang, hypericum, ichthyol, immortelle, ipecac, job's tears, jujube, kola extract, LANACHRYS 28 (available from Lana Tech), lemon oil, lianqiao, licorice root, ligusticum, ligustrum, lovage root, luffa, mace, magnolia flower, manjistha extract, margaspidin, matricin, melatonin, MICROAT IRC (available from Nurture), mints, mistletoe, Modulene (available from Seporga), mono or diglucosides of glabridin, mono or diglucosides of gentian, MTA (5'-deoxy-5'-methythioadenosine), mung bean extract, musk, N-methyl arginine, oat beta glucan, oat extract, orange, panthenol, papain, phenoxyacetic acid, peony bark, peony root, Phytoplenolin (available from Bio Botanica), phytosphingosine, Preregen (available from Pentapharm), purslane, QUENCH T (available from Centerchem), quillaia, red sage, rehmannia, rhubarb, rosemary, rosmarinic acid, royal jelly, rue, rutin, sandlewood, sanqi, sarsaparilla, saw palmetto, SENSILINE (available from Silab), SIEGESBECKIA (available from Sederma), stearyl glycyrrhetinate, Stimutex (available from Pentapharm), storax, strontium nitrate, sweet birch oil, sweet woodruff, tagetes, tea extract, thyme extract, tienchi ginseng, tocopherol, tocopheryl acetate, triclosan, turmeric, urimei, ursolic acid, white pine bark, witch hazel xinyi, yarrow, yeast extract, yucca, and mixtures thereof.

Skin Lightening Actives

Skin lightening actives can be included in the controlled release system of the present invention. Skin lightening actives can actually decrease the amount of melanin in the skin or provide such an effect by other mechanisms and can be included in the controlled release system for stabilizing retinol of the present invention. Skin lightening actives suitable for use herein are described in co-pending patent application Ser. No. 08/479,935, filed on Jun. 7, 1995 in the name of Hillebrand, corresponding to PCT Application No. U.S. Ser. No. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. Ser. No. 95/02809, filed Mar. 1, 1995, published Sep. 8, 1995; all incorporated herein by reference. Non-limiting examples of skin lightening actives useful herein include adapalene, aloe extract, alpha-glycaryl-L-ascorbic acid, aminotyroxine, ammonium lactate, anethole derivatives, apple extract, arbutin, areca catechu L. extract, ascorbic acid, ascorbyl palmitate, azelaic acid, bamboo extract, bearberry extract, bletilla tuber, bupleurum falcatum extract, burnet extract, Burnet Power (available from Barnet Products), butyl hydroxy anisole, butyl hydroxy toluene, butyl resoreinol, Chuanxiong, cola decaballo extract, Dang-Gui, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, esculoside, esculetin, FADE-OUT (available from Pentapharm), Fangfeng, fennel extract, gallic acid and its derivatives, ganodenna extract, gaoben, GATULINE WHITENING (available from Gattlefosse), genistic acid and its derivatives, gentisyl alcohol, glabridin and its derivatives, gluco pyranosyl-1-ascorbate, gluconic acid, glucosamine, glycolic acid, glycyrrhizinic acid, green tea extract, 4-Hydroxy-5-methyl-3[2H]-furanone, hydroquinine, 4 hydroxyanisole and its derivatives, 4-hydroxy benzoic acid derivatives, hydroxycaprylic acid, hyptis extract, inositol ascorbate, kojic acid, kojic dipalnitate, lactic acid, lemon extract, licorice extract, Licorice P-TH (available from Barnet Products), linoleic acid, magnesium ascorbyl phosphate, Melfade (available from Pentapharm), MELAWHITE (available from Pentapharm), Melanostatine DM (available from Laboratories Seporga), morus alba extract, mulberry root extract, niacinamide, 5-octanoyl salicylic acid, parsley extract, phellinus linteus extract, pinon blanco extract, pinon negro extract, piri-piri extract, pyrogallol derivatives, retinoic acid, retinol, retinyl esters (acetate, propionate, palmitate, linoleate), 2,4 resorcinol derivatives, 3,5 resorcinol derivatives, rose fruit extract, rucinol, salicylic acid, Song-Yi extract, Sophora Powder (available from Barnet Products), 4-thioresorein, 3,4,5 trihydroxybenzyl derivatives, tranexamic acid, tyrostat (Rumex Extract available from Fytokem), Tyroslat 10,11 (available from Fytokem), vanilla derivatives, vitamin $D_3$ and its analogs, and mixtures thereof.

Sunscreen Actives

Sun screen agents can be included in the controlled release system of the present invention. The term "sunscreen agent" as used herein defines ultraviolet ray-blocking compounds exhibiting absorption within the wavelength region between about 290 and about 400 nm. Sunscreens can be classified into five groups based upon their chemical structure: para-amino benzoates; salicylates; cinnamates; benzophenones; and miscellaneous chemicals including menthyl anthranilate and digalloyl trioleate. Inorganic sunscreens can also be used including titanium dioxide, zinc oxide, iron oxide and polymer particles such as those of polyethylene, polymethylmethacrylates and polyamides.

A wide variety of conventional sunscreening agents are suitable for use in the present invention as described in Segarin et al., at Chapter VIII, Pages 189 et seq., "Cosmetics Science and Technology", the disclosure of which is incorporated herein by reference. Specific suitable sunscreening agents include, for example: p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxy-naphthoic acid and its salts, o- and p-hydroxybiphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, and the like.

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Non-limiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Still other useful sunscreens include aminobenzoic acid (PABA), benzylidene camphor, butyl methoxy dibenzoyl methane, diethanolamine p-methoxycinnamate, dioxybenzone, ethyl dihydroxypropyl (PABA), glyceryl aminobenzoate, homomenthyl salicylate, isopropyl dibenzoyl methane, lawsone and dihydroxyacetone, menthyl anthranilate, methyl anthranilate, methyl benzylidene camphor, octocrylene, octyl dimethyl (PABA), octyl methoxycinnamate, oxybenzone, 2-phenylbenzimidazole-5-sulfonic acid, red petrolatum, sulisobenzone, titanium dioxide, triethanolamine salicylate, zinc oxide, and mixtures thereof. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)- methylaminobenzoic acid ester of 4-(2-hydroxyethoxy) dibenzoylmethane, and mixtures thereof.

Exact amounts of sunscreens which can be employed will vary depending upon the sunscreen chosen and the desired Sun Protection Factor (SPF) to be achieved. SPF is a commonly used measure of photoprotection of a sunscreen against erythema. See Federal Register, Vol. 43, No. 166, pp. 38206–38269, Aug. 25, 1978, which is incorporated herein by reference in its entirety.

Anti-itch Ingredients

Anti-itch ingredients can be included in the controlled released system of the present invention. Non-limiting examples of anti-itch ingredients which are useful in the compositions of the present invention are those selected from the group consisting of Stimutex (available from Pentapharm); Takanal (available from Ikeda-Distributer); Ichthyol (available from International Sourcing-Distributor); Oxygenated Glyceryl Triesters (available from Seporgia) and mixtures thereof.

Antioxidants

The controlled release system of the invention can also contain other antioxidants including those well known in the art. Representative antioxidants include vitamin E, tocopheryl acetate, betaglucan, coenzyme Q10, representative formula $CH_3C_6(O)_2(OCH_3)_2)CH_2CH:C(CH_3)CH_2!_nH$, butylated hydroxy toluene (BHT), butylated hydroxy anisole BHA, superoxide dismutose, propylgallate, and the like.

Skin Conditioners

The controlled release system of the present invention can also contain other skin conditioners, moisturizers and surfactants can be included as additives. Illustrative conditioners include mineral oil, petrolatum, vegetable oils (such as soybean or maleated soybean oil), dimethicone, dimethicone copolyol, cationic monomers and polymers (such as guar hydroxypropyl trimonium chloride and distearyl dimethyl ammonium chloride) as well as combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Fragrances

A fragrance can be included in the controlled release carrier system of the present invention. The fragrance that can be encapsulated in the carrier system of the present invention can be any odoriferous material and can be selected according to the desires of the fragrance creator. In general terms, such fragrance materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery uses, including materials such as aldehydes, ketones, esters, and the like. More commonly, naturally occurring plant and animal oils and exudates comprising complex mixtures of various chemical components are known for use as fragrances, and such materials can be used herein. Fragrances useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention comprise, for example the high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to skin. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

VI. Processing Method

VI.A. Nanospheres

The encapsulated active agent in the nanospheres of the present invention can be prepared by the steps of (1) heating hydrophobic materials to a temperature above the melting point to form a melt, (2) dissolving or dispersing at least one of an active agent fragrance in the melt, (3) dissolving or dispersing a conditioning agent in the melt, (4) emulsifying the melt in the aqueous phase; and (5) cooling the dispersion to ambient temperature to form a fine suspension.

A fragrance or other active ingredients can be incorporated into the hydrophobic solid nanospheres. Preferably, about 1% to about 80% of and more preferably about 1% to about 60% by weight of the active agents are used in forming the nanospheres.

VI.B. Microspheres

The controlled release system of the present invention can be prepared by the steps of (a) incorporating a conditioning agent, a fragrance, and optionally other active agents into the hydrophobic interior of the nanospheres, (b) forming an aqueous mixture comprising the nanospheres and optionally one or more active agents, a same or different fragrance, the cationic charge booster and a water sensitive material, and (c) spray drying the mixture of the present invention to form a dry powder composition. Accordingly, the nanospheres can be encapsulated into the microsphere structure. One or more of the active agents which can be the same or different than the active agents incorporated in the nanosphere can be incorporated into the microsphere structure.

A process for producing the multi component controlled release system includes the following steps:

(i) heating a hydrophobic material to a temperature above the melting point to form a melt;

(ii) dissolving or dispersing a cationic conditioning agent into the melt;

(iii) dissolving or dispersing a first active agent and fragrance into the melt;

(iii) dissolving or dispersing a second active agent and fragrance, a cationic charge booster, and a water sensitive materials, such as, starch derivative, hydrocolloid, natural gums, polyvinyl alcohol, or mixture of thereof, in the aqueous phase and heating it to above the melting temperature of the hydrophobic material;

(iv) mixing the hot melt with the aqueous phase to form an dispersion;

(v) high shear homogenization of the dispersion at a temperature above the melting temperature until a homogeneous fine dispersion is obtained having a sphere size of from about 1 microns to about 2 microns;

(vi) cooling the dispersion to ambient temperature; and (vii) spray drying the emulsified mixed suspension to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high shear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245–265; Barreto, "Spray Dried Perfumes for Specialties, Soap and Chemical Specialties", December 1966; Maleeny, Spray Dried Perfumes, Soap and San Chem, January 1958, pp. 135 et seq.; Flinn and Nack, "Advances in Microencapsulation Techniques", Batelle Technical Review, Vo. 16, No. 2, pp. 2–8 (1967); U.S. Pat. Nos. 5,525,367; and 5,417,153 which are incorporated herein as references.

In one embodiment microspheres are formed by mixing nanospheres incorporating a selected active agent with polyvinyl alcohol, or compositions of polyvinyl alcohol and polysaccharides, under conditions sufficient to encapsulate the nanospheres. Preferably mixing a selected active agent with the polyvinyl alcohol, or compositions of polyvinyl alcohol and polysaccharides, until the emulsion is formed and then spray drying the emulsion to thereby form an encapsulated nanosphere. In the preferred embodiment, the moisture sensitive matrix is formed of a polyvinyl alcohol material at a level from about 1% to about 80%, preferably from about 1% to about 70% by weight of the matrix material with the balance being the amount by weight of active agents and an optimal amount of polysaccharides. In an alternate embodiment, the polyvinyl alcohol is present in the matrix material in an amount of about 1% to about 80% and the weight of the polysaccharides are present in the amount of about 1% to about 80%. In the preferred embodiment, the active agent composition is generally present at a level from about 0.01% to about 80% preferably from about 1% to about 50% by weight of the encapsulated active agent with the balance being the polyvinyl alcohol or polyvinyl alcohol and polysaccharides. Optionally other conventional ingredients known in the art such as preservatives, surfactants, can be used in accordance with the teachings of the present invention. The multi-component spheres of the present invention preferably have size of from about 0.5 micron to about 300 microns, more preferably from about 1 micron to about 200 microns, most preferably from about 2 microns to about 50 microns. The present invention preferably has minimal active agents on the surface of the spheres, preferably less than 1%.

Polyvinyl alcohol is an excellent barrier material to the permeation of the volatile fragrance ingredients, and as a result the controlled release systems of the present invention do not provide perceptible odor in the dry state. Upon wetting by a sufficient amount of aqueous fluid such as a body fluid, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of moisture activated spheres which provide varying rates of diffusion are contemplated. For example, the moisture activated spheres may diffuse at any of the rates of the following:

(i) at steady-state or zero-order release rate in which there is a substantially continuous release per unit of time;
(ii) a first-order release rate in which the rate of release declines towards zero with time; and
(iii) a delayed release in which the initial rate is slow, but then increases with time.

It has been found that a greater amount of polyvinyl alcohol in the matrix provides slower release rate as compared to a matrix including a lesser amount of polyvinyl alcohol in combination with a polysaccharide. For example, a matrix having about 70% to about 80% polyvinyl alcohol has a slower release rate than a matrix having about 30% to about 40% polysaccharide and about 40% to about 50% polyvinyl alcohol. For example, if a high amount of polyvinyl alcohol is used in the matrix, such as in the range of about 70% to about 80%, the matrix provides controlled release of the active agent over an extended period of time from the time the matrix contacts moisture up to forty-eight hours. If polyvinyl alcohol is combined with polysaccharide in the matrix, such as in the amount of 30% to about 40% polyvinyl alcohol and 30% to about 40% of polysaccharide, a greater amount of active agent is released upon contract with moisture to provide a "burst" of the active agent and the active agent is released over a shorter period of time for example from the time the matrix contacts the fluid up to the range of about 6 hours to about twenty-four hours. Typically, the active agent at the surface of the sphere can be released upon contact with the fluid with the remainder of the active agent being either released in a burst if the matrix dissolves or over an extended period of time upon swelling and softening of the matrix.

Nanospheres formed of a hydrophobic material provide a controlled release system in order to release the active agent over an extended period of time by molecular diffusion. Active agents in the hydrophobic matrix of the nanospheres can be released by transient diffusion. The theoretical early and late time approximation of the release rate of the active ingredients dissolved in the hydrophobic matrix of the nanospheres can be calculated from the following equations:

Early Time Approximation $(m_t/m_{sec}) < 0.4$ $$\frac{M_t}{M_\infty} = 4\left(\frac{D_p t}{\pi r^2}\right)^{1/2} - \frac{D_p t}{r^2} \quad (1)$$

$$\frac{dM_t/M_\infty}{dt} = 2\left(\frac{D_p}{\pi r^2 t}\right)^{1/2} - \frac{D_p}{r^2} \quad (2)$$

Late Time Approximation $(m_t/m_\infty) > 0.6$ $$\frac{M_t}{M_\infty} = 1 - \frac{4}{(2.405)^2}\exp\left(\frac{-(2.405)^2 D_p t}{r^2}\right) \quad (3)$$

$$\frac{dM_t/M_\infty}{dt} = 1 - \frac{4D_p}{r^2}\left(\frac{-(2.405)^2 D_p t}{r^2}\right) \quad (4)$$

wherein:
r is the radius of the cylinder,
$m_\infty$ is the amount fragrance released from the controlled release system after infinite time;
$m_t$ is the amount fragrance released from the controlled release system after time t; and
$D_p$ is the diffusion coefficient of the fragrance or aroma chemical in the matrix The release rate for releasing the active agents from the hydrophobic nanospheres is typically slower than the release rate for releasing active agent from the moisture sensitive matrix. The active agents can be selected to be incorporated into either the hydrophobic nanospheres or the moisture sensitive matrix depending on the desired time for release of the active agents. For example, a predetermined first active agent can be incorporated in the moisture sensitive matrix to be released upon wash and a predetermined second active agent can be incorporated in the hydrophobic nanospheres for release over an extended period of time during or after the first agent has been released. For example, the moisture sensitive matrix formed in accordance with the present invention can release the first active agent upon contact with moisture to provide a "burst" with continued release of the first active agent and nanospheres formed in accordance with the present invention can release the active agent depending on the release rate from an initial time such as within few hours, up to a period of few weeks.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Preparation of Controlled Release Systems for Soaps

EXAMPLE 1

The following procedure is used for the preparation of a controlled release system that provides enhanced deposition of a fragrance transition and vitamin E on the skin and sustains their release over an extended period of time. A floral fragrance and vitamin E are encapsulated in the hydrophobic nanospheres. Incroquat behenyl® HE (behenamidopropyl hydroxyethyl dimonium, commercially available from Croda Inc.) is used as a cationic conditioning agent in the hydrophobic nanospheres and the cationic charge booster incorporated in the water sensitive microsphere is polyethyleneimine having an average molecular weight of 1800, commercially available from BASF Corporation under the trade name LUPASOL™ PR815. The nanospheres hydrophobic matrix is candelilla wax, commercially available from Strahl & Pitsch Inc. of West Babylon, N.Y. The microsphere water sensitive matrix is Hi-Cap™ 100 (commercially available from the National Starch and Chemical Company of Bridgewater, N.J.).

100 grams of candelilla wax is placed in an oven at 80 degrees ° C. and allowed to melt. 1500 grams of deionized water are placed into 1 gallon vessel, fitted with an all-purpose silicon rubber heater (Cole-Palmer Instrument Company). 500 grams of Hi-Cap™ 100 (commercially available from the National Starch and Chemical Company of Bridgewater, N.J.) was added to the water and the aqueous solution is heated to 90 degree C. while mixing it with a propeller mixer. The candelilla wax is removed from the oven and 300 grams of floral fragrance (commercially available from Noville Inc. of South-Hackensack, N.J.) and 50 grams of vitamin E (commercially available from JEEN International Corporation of Little Fall, N.J.) are mixed into the melt by hand with a glass rod. 40 grams of incroquat behenyl HE (commercially available from Croda Inc.) are also added to the melt. The fragrance/vitamin E/wax mixture is poured into the aqueous solution and the dispersion and 10 grams of LUPASOL™ PR815 commercially available from BASF Corporation are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 30% floral fragrance and 5% vitamin E encapsulated in the solid hydrophobic nanospheres.

EXAMPLE 2

The following procedure is used for the preparation of a controlled release system that provides fragrance transition (powder floral to mint) as well as delivers jojoba oil for extended period of time. Menthol and jojoba oil are encapsulated in the hydrophobic nanospheres and a powder floral fragrance is encapsulated in the water sensitive microsphere. The nanospheres hydrophobic matrix is Ganex® V-220 (commercially available from the ISP Technologies Inc, of Wayne, N.J.). The microsphere water sensitive matrix is Hi-Cap™ 100 (commercially available from the National Starch and Chemical Company of Bridgewater, N.J.).

100 grams of Ganex® V-220 (commercially available from the ISP Technologies Inc, of Wayne, N.J.) and 50 grams of incroquat behenyl® HE (behenamidopropyl hydroxyethyl dimonium, commercially available from Croda Inc.) are placed in an oven at 60 degrees C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. Ganex® V-220 is removed from the oven and 50 grams of Menthol (commercially available from Noville Inc. of South-Hackensack, N.J.) and 50 grams of jojoba oil (commercially available from JEEN International Corporation of Little Fall, N.J.) are mixed into the melt by hand with a glass rod. The menthol/jojoba oil/Ganex® V-220 mixture is poured into the aqueous solution and the dispersion and 300 grams of a powder floral fragrance (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Massachusetts) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 5% menthol and 5% jojoba oil encapsulated in the solid hydrophobic nanospheres. The controlled release system obtained contains 5% menthol and 5% jojoba oil, 10% Ganex® V-220, 5% incroquat behenyl HE, 30% powder floral fragrance, and 45% water sensitive material.

EXAMPLE 3

The following procedure is used for the preparation of a controlled release system that encapsulates the same fragrance in both the solid hydrophobic nanospheres and the water sensitive microsphere to provide both fragrance "burst" in response to moisture as well as extend fragrance release over a prolonged period of time. The nanospheres hydrophobic matrix is Ganex® V-220 (commercially available from the ISP Technologies Inc, of Wayne, N.J.). The microsphere water sensitive matrix is Hi-Cap™ 100 (commercially available from the National Starch and Chemical Company of Bridgewater, N.J.).

200 grams of Ganex® V-220 (commercially available from the ISP Technologies Inc, of Wayne, N.J.) and 50 grams of incroquat behenyl® HE (behenamidopropyl hydroxyethyl dimonium, a cationic conditioning agent, commercially available from Croda Inc.) are placed in an oven at 60 degrees ° C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. The Ganex® V-220 and cationic conditioning agent are removed from the oven and 100 grams of green fragrance (commercially available from Noville Inc. of South-Hackensack, N.J.) is mixed into the melt by hand with a glass rod. The fragrance/Ganex® V-220 mixture is poured into the aqueous solution and the dispersion and 200 grams of a green fragrance (commercially available from Noville Inc. of South-Hackensack, N.J.) are homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 10% green fragrance encapsulated in the solid hydrophobic nanospheres. The controlled release system obtained contains 10% green fragrance in the nanospheres, 20% Ganex® V-220, 5% incroquat behenyl® HE, 20% green fragrance in the microspheres, and 45% water sensitive material.

Incorporation of the Controlled Release System in Soap Products

EXAMPLE 4

Toilet soaps containing 1% neat fragrance was prepared by mixing 1 gram of the neat green fragrance oil with the soap base followed by milling the mixture to create a soap bar. A toilet soap bar comprising the encapsulated (Example 3) green fragrance was prepared by mixing 3.3 grams of the powder of example 3 with the soap base and creating a soap bar.

The ability of the soap bar to provide fragrance "burst" upon wash as well as long lasting fragrance residue on skin following aging the samples for one month at 45° C. was evaluated by washing hands with the two types of soap prepared, i.e., a control sample comprising the neat oil and the experimental sample comprising the encapsulated fragrance of Example 3.

|  | Fragrance Intensity Upon Wash |
|---|---|
| Neat Fragrance (Control) | 2 |
| Encapsulated Fragrance | 5 |

The results clearly indicate the controlled release system of the present invention has the ability to retain the fragrance during storage and release it upon need in response to moisture, during wash.

|  | Fragrance Intensity on Skin Following Wash | |
|---|---|---|
|  | 2 Hours | 8 Hours |
| Neat Fragrance (Control) | 3 | 1 |
| Encapsulated Fragrance | 7 | 4 |

These results show that skin washed with the control sample, comprising the neat fragrance, had very low odor intensity. The skin washed the soap bar comprising the encapsulated fragrance had higher odor intensity and odor intensity of the skin washed the soap bar comprising the encapsulated fragrance, 8 hours after wash, was significantly higher than that washed with the control sample. Thus, the controlled release system of the present invention sustains the release of the fragrance over an extended period of time.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A controlled delivery system for soap comprising:
   a plurality of solid positively charged nanospheres, each of said solid nanospheres comprising an effective amount of a first active agent said plurality of nanospheres being encapsulated in a moisture sensitive microsphere, said moisture sensitive microsphere is formed of a moisture sensitive matrix material and a second active agent encapsulated in said moisture sensitive matrix material wherein said first active agent is the same or different than said second active agent, said first active agent and said second active agent is a fragrance and one or more of a vitamin, antimicrobial agent, antifungal agent, anti-inflammatory agent, anti-acne agent, cosmetic soothing active, skin lightening active, sunscreen active, anti-itch active, antioxidant or skin conditioner and wherein said moisture sensitive matrix material releases said second active agent upon contact with moisture.

2. A controlled delivery system for soap comprising:
   a plurality of solid positively charged nanospheres, each of said solid nanospheres comprising an effective amount of a first active agent said plurality of nanospheres being encapsulated in a moisture sensitive microsphere, said moisture sensitive microsphere is formed of a moisture sensitive matrix material and a second active agent encapsulated in said moisture sensitive matrix material wherein said system comprises about 1% to about 50% by weight of said hydrophobic matrix material, about 1% to about 50% of said moisture sensitive matrix, from about 0% to about 10% by weight of a cationic charge booster, from about 0.01% to about 10% by weight first and second cationic conditioning agent, and said active agent comprising from about 1% to about 50% by weight fragrance and from 0% to 50% by weight of the nanospheres of an active ingredient and wherein said moisture sensitive matrix material releases said second active agent upon contact with moisture.

3. A controlled delivery system for soap comprising:
a plurality of solid positively charged nanospheres, each of said solid nanospheres comprising an effective amount of a first active agent, said plurality of nanospheres being encapsulated in a moisture sensitive microsphere, said moisture sensitive microsphere is formed of a moisture sensitive matrix material wherein said moisture sensitive matrix material is formed of polyvinyl alcohol in an amount of about 1% to about 80% by weight of the matrix material.

4. A controlled delivery system for soap comprising:
a plurality of solid positively charged nanospheres, each of said solid nanospheres comprising an effective amount of a first active agent, said plurality of nanospheres being encapsulated in a moisture sensitive microsphere, said moisture sensitive microsphere is formed of a moisture sensitive matrix material wherein said nanoparticle comprises a cationic conditioning agent.

5. The system of claim 4 wherein said cationic conditioning agent is selected from the group consisting of cationic quaternary ammonium salts, acyclic quaternary ammonium salts having at least two $C_8$–$C_{30}$ alkyl chains, cyclic quaternary ammonium salts of the imidazolinium type, diamide quaternary ammonium salts, biodegradable quaternary ammonium salts, tertiary fatty amines having at least one $C_8$ to $C_{30}$ chains, carboxylic acids, esters of polyhydric alcohols, fatty alcohols, ethoxylated fatty alcohols, alkylphenols, ethoxylated alkylphenols, ethoxylated fatty amines, ethoxylated monoglycerides, ethoxylated diglycerides, mineral oil, silicone oil, silicone surfactants and mixtures thereof.

6. The system of claim 4 wherein said cationic conditioning agent is selected from the group consisting of ditallowdimethyl ammonium methylsulfate, di(hydrogenated tallow) dimethyl ammonium methylsulfate, distearyldimethyl ammonium methylsulfate, dicocodimethyl ammonium methylsulfate, di(hydrogenated tallow)dimethyl imidazolinium methylsulfate, 1-ethylene-bis(2-tallow 1-methyl) imidazolinium methylsulfate, methyl-bis(hydrogenated tallow amidoethyl)-2-hydroxyethyl ammonium methyl sulfate, methyl bis(tallowamidoethyl)-2-hydroxypropyl ammonium methylsulfate, N,N-di (tallowoyl-oxy-ethyl)-N,N,-dimethyl ammonium methyl sulfate, N,N-di (tallowoyl-oxy-propyl)-N,N-dimethyl ammonium methyl sulfate, tallow-dimethylamine, cyclic amines, 1-(hydrogenated tallow) amidoethyl-2-(hydrogenated tallow)imidazoline and mixtures thereof.

7. The system of claim 4 wherein said cationic conditioning agent is selected from the group consisting of: behenyltrimethylammonium chloride; ditallowdimethylammonium methylsulfate; ditallowdimethylammonium chloride; methyl(1) stearylamidoethyl (2) stearylimidazolinium methosulfate; methyl(1)stearylamidoethyl(2) stearylimidazolinium chloride; N,N-di(tallowyl-oxy-ethyl)-N,N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium chloride; N,N-di(canolyl-oxy-ethyl)-N-methyl, N-(2-hydroxyethyl) ammonium chloride; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl)-N,N-dimethyl ammonium chloride; N,N,N-tri(tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; 1,2-dicanolyloxy-3-N,N,N-trimethylammoniopropane chloride; methyl-1-tallowamidoethyl-2-tallowimidazolinium methylsulfate; monotallowtrimethylammonium chloride; mono(hydrogenated tallow) trimethylammonium chloride; palmityltrimethyl ammonium chloride; soyatrimethylammonium chloride; dimethylstearylbenzyl ammonium chloride and mixtures thereof.

8. A controlled delivery system for soap comprising:
a plurality of solid positively charged nanospheres, each of said solid nanospheres comprising an effective amount of a first active agent, said plurality of nanospheres being encapsulated in a moisture sensitive microsphere, said moisture sensitive microsphere is formed of a moisture sensitive matrix material wherein said microparticle comprises a cationic charge booster.

9. The system of claim 8 wherein said cationic charge booster is selected from the group consisting of a quaternary ammonium compound, polyvinyl amine, polyalkyleneimine, and poly-quaternary ammonium compound.

10. The system of claim 8 wherein said cationic charge boosters comprises polyethyleneimine having an average molecular weight of 1,800.

11. A controlled delivery system for soap comprising:
a plurality of solid positively charged nanospheres, each of said solid nanospheres comprising an effective amount of a first active agent, said plurality of nanospheres being encapsulated in a moisture sensitive microsphere, said moisture sensitive microsphere is formed of a moisture sensitive matrix material wherein said nanoparticle comprises a cationic conditioning agent and said microparticle comprises cationic charge booster.

12. The system of claim 11 wherein said cationic conditioning agent is selected from the group consisting of cationic quaternary ammonium salts, acyclic quaternary ammonium salts having at least two $C_8$–$C_{30}$ alkyl chains, cyclic quaternary ammonium salts of the imidazolinium type, diamide quaternary ammonium salts, biodegradable quaternary ammonium salts, tertiary fatty amines having at least one $C_8$ to $C_{30}$ chains, carboxylic acids, esters of polyhydric alcohols, fatty alcohols, ethoxylated fatty alcohols, alkylphenols, ethoxylated alkylphenols, ethoxylated fatty amines, ethoxylated monoglycerides, ethoxylated diglycerides, mineral oil, silicone oil, silicone surfactants and mixtures thereof.

13. The system of claim 11 wherein said cationic charge booster is selected from the group consisting of a quaternary ammonium compound, polyvinyl amine, polyalkyleneimine, and poly-quaternary ammonium compound.

14. An article of manufacture comprising a controlled delivery system for soap comprising a plurality of solid positively charged nanospheres, each of said solid nanospheres comprising an effective amount of a first active agent said plurality of nanospheres being encapsulated in a moisture sensitive microsphere, said moisture sensitive microsphere is formed of a moisture sensitive matrix material wherein said article is a soap bar.

15. A method for forming a controlled delivery system for soap comprising a plurality of solid positively charged nanospheres, each of said solid nanospheres comprising an effective amount of a first active agent said plurality of nanospheres being encapsulated in a moisture sensitive microsphere, said moisture sensitive microsphere is formed of a moisture sensitive matrix material, wherein the method comprises the steps of:

heating a hydrophobic material to a temperature above the melting point to form a melt;

dissolving or dispersing a cationic conditioning agent into the melt;

dissolving or dispersing said first active agent into the melt;

dissolving or dispersing a second active agent and fragrance, a cationic charge booster, and a water sensitive materials;

mixing the hot melt with the aqueous phase to form an dispersion; and high shear homogenization of the dispersion at a temperature above the melting temperature until a homogeneous fine dispersion is obtained, cooling the dispersion to ambient temperature; and spray drying the emulsified mixed suspension to form a dry powder composition.

16. A method for forming a controlled delivery system for soap comprising a plurality of solid positively charged nanospheres, each of said solid nanospheres comprising an effective amount of a first active agent said plurality of nanospheres being encapsulated in a moisture sensitive microsphere, said moisture sensitive microsphere is formed of a moisture sensitive matrix material and a second active agent encapsulated in said moisture sensitive matrix material, wherein said moisture sensitive matrix material releases said second active agent upon contact with moisture, wherein the method comprises the steps of:

heating a hydrophobic material to a temperature above the melting point to form a melt;

dissolving or dispersing a cationic conditioning agent into the melt;

dissolving or dispersing said first active agent into the melt;

dissolving or dispersing said second active agent, a cationic charge booster, and a water sensitive material in the aqueous phase and heating it to above the melting temperature of the hydrophobic material;

mixing the hot melt with the aqueous phase to form an dispersion;

high shear homogenization of the dispersion at a temperature above the melting temperature until a homogeneous fine dispersion is obtained;

cooling the dispersion to ambient temperature; and spray drying the emulsified mixed suspension to form a dry powder composition.

* * * * *